(12) United States Patent
Maertz

(10) Patent No.: US 10,881,304 B2
(45) Date of Patent: Jan. 5, 2021

(54) EXERCISE AND COMMUNICATION SYSTEM AND ASSOCIATED METHODS

(71) Applicant: Richard J. Maertz, Capistrano Beach, CA (US)

(72) Inventor: Richard J. Maertz, Capistrano Beach, CA (US)

( * ) Notice: Subject to any disclaimer, the term of this patent is extended or adjusted under 35 U.S.C. 154(b) by 454 days.

(21) Appl. No.: 15/713,437

(22) Filed: Sep. 22, 2017

(65) Prior Publication Data

US 2018/0008151 A1    Jan. 11, 2018

Related U.S. Application Data

(62) Division of application No. 14/474,239, filed on Sep. 1, 2014, now Pat. No. 9,782,084, and a division of
(Continued)

(51) Int. Cl.
*A61B 5/0205* (2006.01)
*G16H 40/67* (2018.01)
(Continued)

(52) U.S. Cl.
CPC .......... *A61B 5/0205* (2013.01); *A61B 5/0004* (2013.01); *A61B 5/083* (2013.01); *A61B 5/1118* (2013.01); *A61B 5/14551* (2013.01); *A61B 5/486* (2013.01); *A61B 5/681* (2013.01); *A61B 5/6898* (2013.01); *A61B 5/7246* (2013.01); *A61B 5/7405* (2013.01);
(Continued)

(58) Field of Classification Search
CPC ..... A61B 5/0205; A61B 5/0004; A61B 5/083; A61B 5/1118; A61B 5/14551; A61B 5/486; A61B 5/681; A61B 5/6898; A61B 5/7246; A61B 5/7405; A61B 5/7475; A61B 5/02416; A61B 5/0836; G16H 20/30; G16H 40/67; A63B 24/0062; A63B 24/0075; A63B 71/0622; A63B 2024/0081; A63B 2024/0096; A63B 2220/30; A63B 2225/50; A63B 2230/06; A63B 2230/205; A63B 2230/207; A63B 2230/75; G06F 19/3481
See application file for complete search history.

(56) References Cited

U.S. PATENT DOCUMENTS 5,675,811 A * 10/1997 Broedner ............ G06F 13/4291
                                                     710/104
6,247,470 B1 * 6/2001 Ketchedjian ...... A61M 16/0666
                                                     128/200.28
(Continued)

*Primary Examiner* — Manuel L Barbee
(74) *Attorney, Agent, or Firm* — PATNSTR®, APC; Tom Brody; Peter Jon Gluck, Esq.

(57) ABSTRACT

An exercise and communications system includes an interactive device, a remote device, and an external device, wherein the interactive device is configured to gather data relating to a user of the system and transmit the same to the remote device, and the remote device is configured to provide analyze the data and transmit a response to the interactive device, which in turn communicates the response to the user and additionally communication with an external device for retrieval of instructions, programs, and data, inter alia. An exercise and communications system facilitates communication between a plurality of users, each having an interactive device and a remote device.

16 Claims, 8 Drawing Sheets

Related U.S. Application Data application No. 12/827,888, filed on Jun. 30, 2010, now Pat. No. 8,821,350.

(60) Provisional application No. 61/222,749, filed on Jul. 2, 2009.

(51) Int. Cl.

| | | |
|---|---|---|
| *G16H 20/30* | (2018.01) | |
| *A61B 5/083* | (2006.01) | |
| *A61B 5/00* | (2006.01) | |
| *A61B 5/11* | (2006.01) | |
| *A61B 5/1455* | (2006.01) | |
| *A63B 24/00* | (2006.01) | |
| *A63B 71/06* | (2006.01) | |
| *A61B 5/024* | (2006.01) | |

(52) U.S. Cl.
CPC ........ *A61B 5/7475* (2013.01); *A63B 24/0062* (2013.01); *A63B 24/0075* (2013.01); *A63B 71/0622* (2013.01); *G16H 20/30* (2018.01); *G16H 40/67* (2018.01); *A61B 5/02416* (2013.01); *A61B 5/0836* (2013.01); *A63B 2024/0081* (2013.01); *A63B 2024/0096* (2013.01); *A63B 2220/12* (2013.01); *A63B 2220/30* (2013.01); *A63B 2225/50* (2013.01); *A63B 2230/06* (2013.01); *A63B 2230/205* (2013.01); *A63B 2230/207* (2013.01); *A63B 2230/75* (2013.01)

(56) References Cited

U.S. PATENT DOCUMENTS

| | | | |
|---|---|---|---|
| 2004/0186390 A1* | 9/2004 | Ross | A61B 5/682 |
| | | | 600/532 |
| 2005/0124463 A1* | 6/2005 | Yeo | A63B 69/00 |
| | | | 482/8 |

* cited by examiner

EXERCISE AND COMMUNICATION SYSTEM AND ASSOCIATED METHODS

CROSS-REFERENCE TO RELATED APPLICATION

This application is a Divisional of U.S. patent Ser. No. 14/474,239, filed Sep. 1, 2014, which is a Divisional of U.S. Ser. No. 12/827,888 filed Jun. 30, 2010, now U.S. Pat. No. 8,821,350, which claims full Paris Convention priority on U.S. Provisional Ser. No. 61/222,749, filed on Jul. 2, 2009, the entire content of each is incorporated herein by reference.

BACKGROUND

This disclosure relates to interactive exercise devices and systems for communication between components of the same as well as users and communications between related interactive exercise devices.

SUMMARY

Briefly stated an exercise and communications system includes an interactive device, a remote device, and an external device, wherein the interactive device is configured to gather data relating to a user of the system and transmit the same to the remote device, and the remote device is configured to analyze the data and transmit a response to the interactive device, which in turn communicates the response to the user and additionally communicates with an external device for retrieval of instructions, programs, and data, inter alia. An exercise and communications system facilitates communication between a plurality of users, each having an interactive device and a remote device.

According to embodiments of the present disclosure, a system is disclosed, which may collect and transmit wirelessly biometric feedback from an individual (e.g., walkers, joggers, which could be integrated with a pedometer), while using a biometric data probe (e.g., earpiece), or to a group of individuals (e.g., track athletes, cross country, skiers, cyclists, swimmers, water polo players, baseball players, football players, soccer players, field hockey players, ice hockey players, rowers, etc.), whereby a centralized "coaching data collection and communication system" would facilitate monitoring the athletes biometric and training goals or the patients biometric feedback including temperature, heart rate, oxygen saturation, end tidal carbon dioxide, etc., and also allow a coach or health care professional to communicate directly with an individual or to a specific and select group of individuals.

According to embodiments of the present disclosure, GPS support may be provided as would all of the data collection (e.g., time, distance, calorie consumption, speed, calculated $VO_2$ Max. Value, work load, strength, etc.) from the individual and/or the team which would also provide for complete communications capabilities including two-way communications to include cell transmissions for phone and entertainment, with audio message alerts preset by the athlete or coach for training zone high and low limits whereby customized training regimen options could be selected by the individual or group, and/or downloaded via our training systems to maximize the training experience. A normal training regimen can be set by the individual by inputting the individual's gender, weight, age, etc. Customized training can be input by the individual. Additionally, a specific "stamina test" regimen can be selected for the individual or for the group. The "coach" can access the program and monitor and change the workout, either up or down to make it harder or easier. A competition could be developed by a community of users of the system, the "Bio-Pod community," for example, broadcasting worldwide via Web TV.

According to embodiments of the present disclosure, an interactive device comprises one or more sensors configured to sense at least one physiological parameter of a user during an activity. The sensors may be adapted to sense the at least one physiological parameter from any part of the user's body, including but not limited to a finger, ear, mouth, arm, leg, trunk. The at least one physiological parameter sensed by the interactive device corresponds to a measurable aspect of an activity of the user and may be at least one of heart rate, oxygen saturation and end tidal carbon dioxide. A remote interface is configured to communicate data corresponding to the at least one physiological parameter to a remote device during the activity, and further configured to receive from the remote device a response corresponding to the at least one physiological parameter. The response is determined by the remote device based on whether the at least one physiological parameter is within a predetermined criteria.

A user interface configured to communicate the response to the user also is provided. The user interface may comprise an audio speaker configured to transmit audible messages to the user. The remote device is configured to be supported by the user during an activity and may be a watch, a cell phone, a personal digital assistant or an arm mount fixation device. The one or more sensors and the remote device may be integrated in a single housing configured to be disposed within an ear of the user, and the end tidal carbon dioxide sensor may be mounted on a tube located in front of the user's mouth. The interactive device may be in wireless communication with the remote interface. The remote device may be in operative communication with an external device, and the external device may be, among other things, an entertainment system, a computing system, a video game console, and/or Web TV.

According to embodiments of the present disclosure, methods performed by a remote device in data communication with an interactive device comprise, in combination, determining a selected exercise mode, receiving, from an interactive device, data corresponding to a parameter sensed by the interactive device, comparing the data to a predetermined criteria associated with the selected exercise mode, selecting a predetermined response based on whether the data is within the criteria associated with the selected exercise mode, and transmitting the predetermined response to the interactive device. The predetermined response is communicated to the user via the interactive device, and may be communicated via an audio output device of the interactive device.

The selected exercise mode may be selected by a user from among a plurality of exercise modes. The parameter sensed by the interactive device corresponds to a physiological parameter of the user, and the physiological parameter may be at least one of heart rate, temperature, oxygen saturation and end tidal carbon dioxide. The remote device and interactive device may be integrated into a single housing configured to be disposed within an ear of the user. Embodiments may further comprise transmitting the data corresponding to the parameter to an external device and/or retrieving associated responses and criteria from an external device. The data may be downloaded and stored in an external device such as a personal computer, a log card, a memory stick or other device capable of storing data. The external device may distribute the data corresponding to the parameter and/or a response to at least one other user.

According to embodiments of the present disclosure, an exercise and communications system comprises an interactive device configured to collect biometric information from any part of a first user's body, e.g., a first user's ear during an activity, a remote device in operative communication with the interactive device and an external device in operative communication with the remote device. The interactive device and the remote device may be integrated into a single housing configured to be clipped to or disposed within the user's ear. The external device receives the collected biometric information from the remote device and may include an entertainment system, a computing system, the internet, a video game console, Web TV and/or a second user. The interactive device and/or the remote device responds to the collected biometric information by effecting alterations to the activity of the first user. The external device responds to the collected biometric information by transmitting information to the interactive device and/or providing real time audio communication to the first user during the activity. The biometric information may be collected by pulse oximetry and may be heart rate, temperature, end tidal carbon dioxide and/or oxygen saturation. Likewise, those helpful and other data are included within this subset according to the teachings of the instant disclosure.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The present invention has taken a lifetime of sports and fitness training and combined it with modern technology to provide a new system for super-motivated users. According to embodiments of the present disclosure, an exercise and communications system is disclosed, which may collect and transmit wirelessly biometric feedback from an individual, while using a biometric data probe (e.g., earpiece), or to a group of individuals (e.g., track athletes, cross country, skiers, cyclists, swimmers, water polo players, baseball players, football players, soccer players, field hockey players, ice hockey players, etc.), whereby a centralized "coaching data collection and communication system" would facilitate monitoring the athletes' biometric and training goals or the patients biometric feedback including heart rate, temperature, oxygen saturation, end tidal carbon dioxide, etc., and also allow a coach or health care professional to communicate directly with an individual or to a specific and select group of individuals.

According to embodiments of the present disclosure, GPS support may be provided as would all of the data collection (e.g., time, distance, calorie consumption, speed, calculated $VO_2$ Max. Value, etc.) from the individual and/or the team which would also provide for complete communications capabilities including two-way communications to include cell transmissions for phone and entertainment, with audio message alerts preset by the athlete or coach for training zone high and low limits whereby customized training regimen options could be selected by the individual or group, and/or downloaded via our training systems to maximize the training experience.

Figure 1:
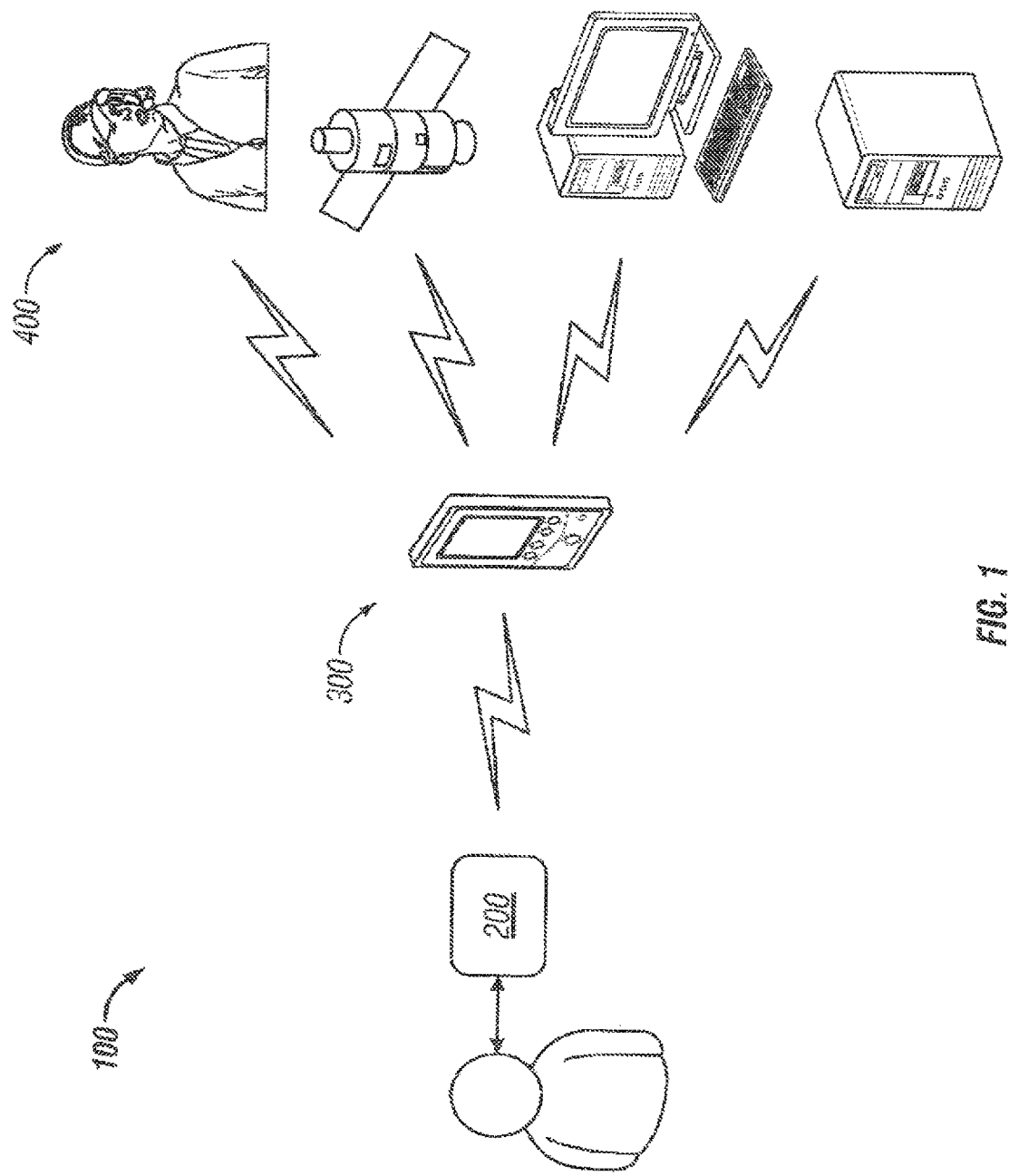
FIG. 1 is a schematic block diagram illustrating various system components configured to operate and communicate as used by a single user, according to embodiments of the present disclosure.

According to embodiments, and as shown in FIG. 1, an exercise and communications system 100 is shown, wherein interactive device 200 may be configured to interface with a remote device 300, which may be configured to interface with an external device 400.

According to embodiments, interactive device 200 may be a non-invasive device to facilitate and support an exercise training and bio-feedback system. For example, interactive device 200 may be or include hand grips with sensors, a chest strap, a pulse oximeter device to obtain heart-rate from a finger or ear lobe of a user. Interface device 200 may be configured to sense physiological parameters relating to the user as well other data relating to the environment of the user, and may be configured to provide information to the user during an activity.

According to embodiments, remote device 300 may include a device that may be supported by or near a user during an activity. For example, remote device 300 may include a watch, a cell phone, a personal digital assistant, an arm mount fixation device, a device configured to be supported by a user, a device configured to be supported by an exercise device (e.g., a stationary or non-stationary bicycle), or other communication that provides enhanced features via a communications interface that links to interactive device 200. According to embodiments, interactive device 200 and remote device 300 may be separate while maintaining a communications link or may be integrated into a single housing.

According to embodiments, interactive device 200 may collect data regarding a user, a physiological parameter of the user, the user's performance during an activity, or the environment of the user. For example, interactive device 200 may monitor a user's heart rate, temperature, oxygen saturation, end tidal carbon dioxide, etc. or any combination thereof. Collection of various combinations of physiological parameters could be combined with communication features to create models tailored to the desires of different types of users. For example, a "sport" model might comprise collection of heart rate data and communication features. A "competition" model for serious athletes might comprise collection of heart rate data and oxygen saturation data together with communication features. A "pro" model for professional athletes might comprise collection of heart rate data, oxygen saturation data and end tidal carbon dioxide data together with communication features.

According to embodiments, interactive device 200 may monitor the user's physiological parameters, physical performance, location, global position, rate of travel, pace of movement, etc. Information gathered by interactive device 200 may be stored or communicated to remote device 300. Remote device 300 may analyze, process, or manipulate the information from interface device 200 and store it or provide a response to interactive device 200, causing interactive device 200 to provide a feature to the user. The feature provided to the user may be a report, a warning, an instruction, music, or other response to the information exchanged between interactive device 200 and remote device 300. For example, interactive device 200 may notify a user when interactive device 200 is out of range of remote device 300, when the user is not achieving target goals, or when the user is outside predetermined safety parameters. The user can input into the interactive device 200 the desired training and/or safety parameters including target goals and/or desired heart rate. The user can input these data from a computer or web-based interfaces, and the data can be wirelessly downloaded to the interactive device 200. Additionally the system offers safety features for both exercise fitness training and for healthcare users.

According to embodiments, at least one of interactive device 200 and remote device 300 may respond to data collected by effecting alterations to the activity or environment of the user. For example, where a bicycle is used, at least one of interactive device 200 and remote device 300 may alter resistance or other feature of the bicycle relative to the action of the user. Where a treadmill is used, at least one of interactive device 200 and remote device 300 may alter the speed, incline, or other features of the treadmill. Such adjustments may be made to attempt to bring the user into a predetermined target range of desired values corresponding to the collected data. Other exercise machines may be used such as rowing or "erg" machines, and any other developed technology of existing machines.

According to embodiments, a bicycle configured for use with exercise and communications system 100 may include a resistance device responsive to commands from a user or components of exercise and communications system 100. The resistance device may include a disk brake mechanism with magnets with variable and controllable distance from the disk or steel or other durable material. The magnets may create a simplistic magnetic resistance mechanism that can be controlled wirelessly or by a thumb shifter to easily increase or decrease the resistance by adjusting how near or far away the magnets come to the disk, thereby increasing the drag and the workload which would force the user to increase their work rate and subsequent increased heart-rate, allowing them to customize their workout based on heart-rate and their desired "Target Zone" for training. Such adjustments may be user controlled or automated based on calculations, commands, and responses of components of exercise and communications system 100. Alternatively, the adjustments may be controlled wirelessly by the "coach." The resistance provided by the disk brake mechanism may provide a more rigorous workout without requiring the user to achieve a high speed of motion. Such a disk brake mechanism may be configured for a stationary or non-stationary bicycle.

According to embodiments, a user may use one or both of interactive device 200 and remote device 300 to choose a mode. (e.g., "Running", "Jogging", "Walking", "Swimming", "Exercising at home or at a health training facility", "Cycling", etc.). The modes may be applications or "apps" downloadable from the internet and may be stored in interactive device 200. Each mode may have a predetermined or user-determinable set of criteria such as target goals, safe range of physiological parameters, etc. Analysis of data collected by interactive device 200 may correspond to these criteria.

Figure 5:
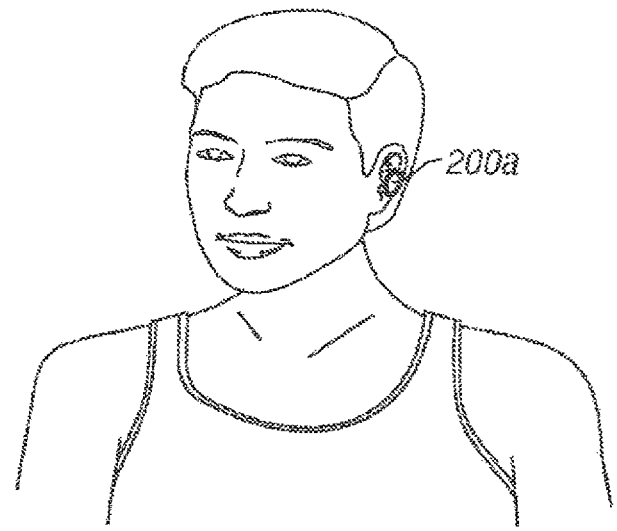
FIG. 5 is a perspective view of an interactive device, according to embodiments of the present disclosure.
Figure 6:
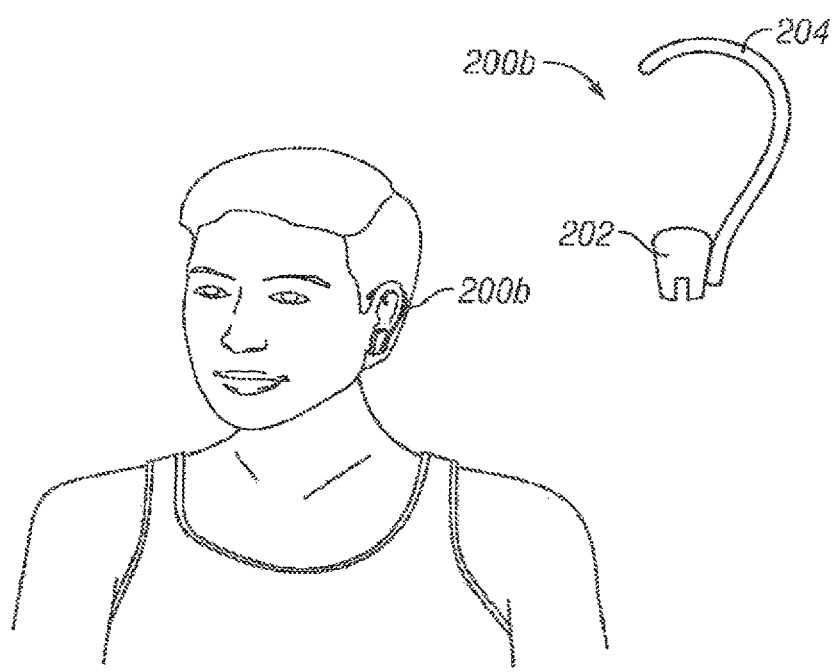
FIG. 6 is a perspective view of an interactive device, according to embodiments of the present disclosure.

According to embodiments, interactive device 200 may be a device configured to be disposed within an ear of the user or clipped or otherwise mounted to an ear of the user and to collect bio-metric vital sign feedback from the user's ear and/or earlobe and provide continuous or intermittent communication (e.g., audio) to the user during an activity. FIG. 5 shows an exemplary embodiment of an interactive device 200a designed to be disposed within the user's ear. FIG. 6 shows an exemplary embodiment of an interactive device 200b designed to be clipped or mounted to the user's ear. Interactive device 200b may include one or more of ear lobe clip 202 and/or over-the-ear mounting member 204. Such interactive device may be an earpiece that has Bluetooth functionality. It should be understood that such interactive devices 200 may be employ any known method of mounting to or within an ear including combinations of in-ear and over-the-ear mounting designs.

Figure 7:
FIG. 7 is a perspective view of an interactive device and carbon dioxide sensor, according to embodiments of the present disclosure.

As shown in FIG. 7, interactive device 200 may also include a device configured to be positioned in front of the mouth of the user to sense carbon dioxide levels during expiration. In exemplary embodiments, such a device may comprise one or more tubes 210 coupled to the ear device mounting a carbon dioxide sensor 212 and extending to a location in front of the mouth of the user. In this way, all biometric sensing functions are incorporated into a single earpiece.

Figure 8:
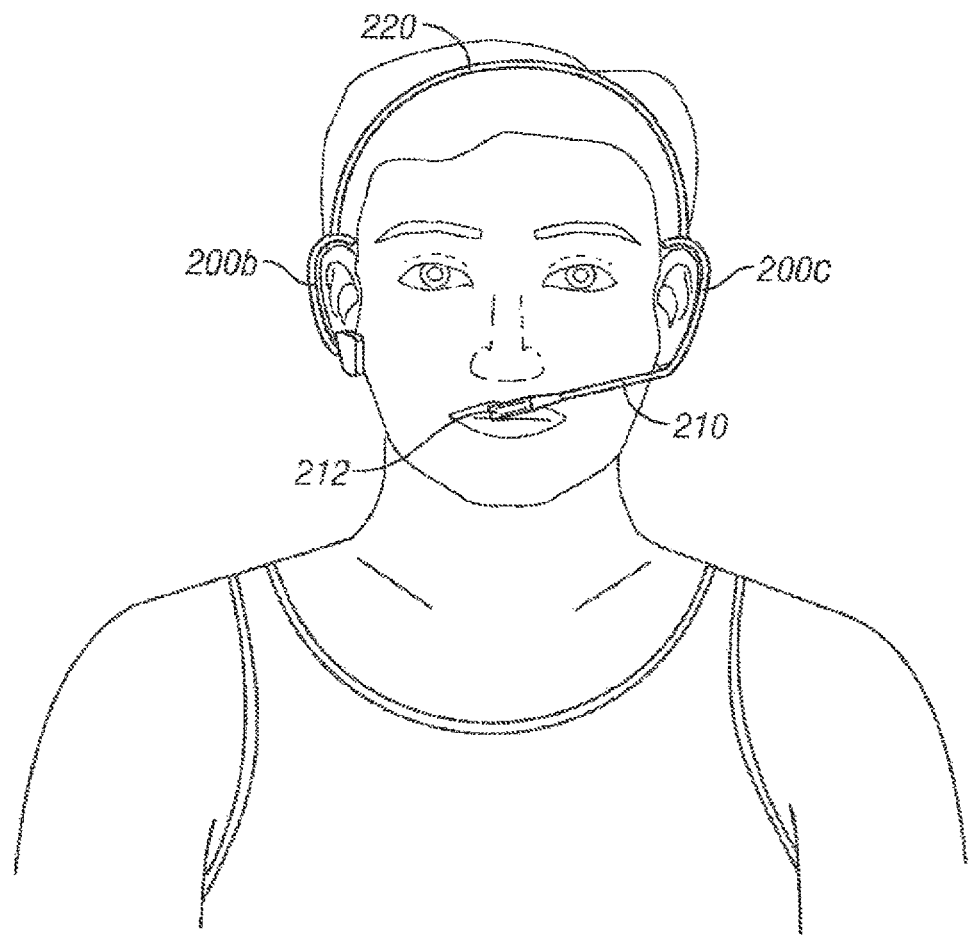
FIG. 8 is a perspective view of an interactive device and carbon dioxide sensor, according to embodiments of the present disclosure.
Figure 9:
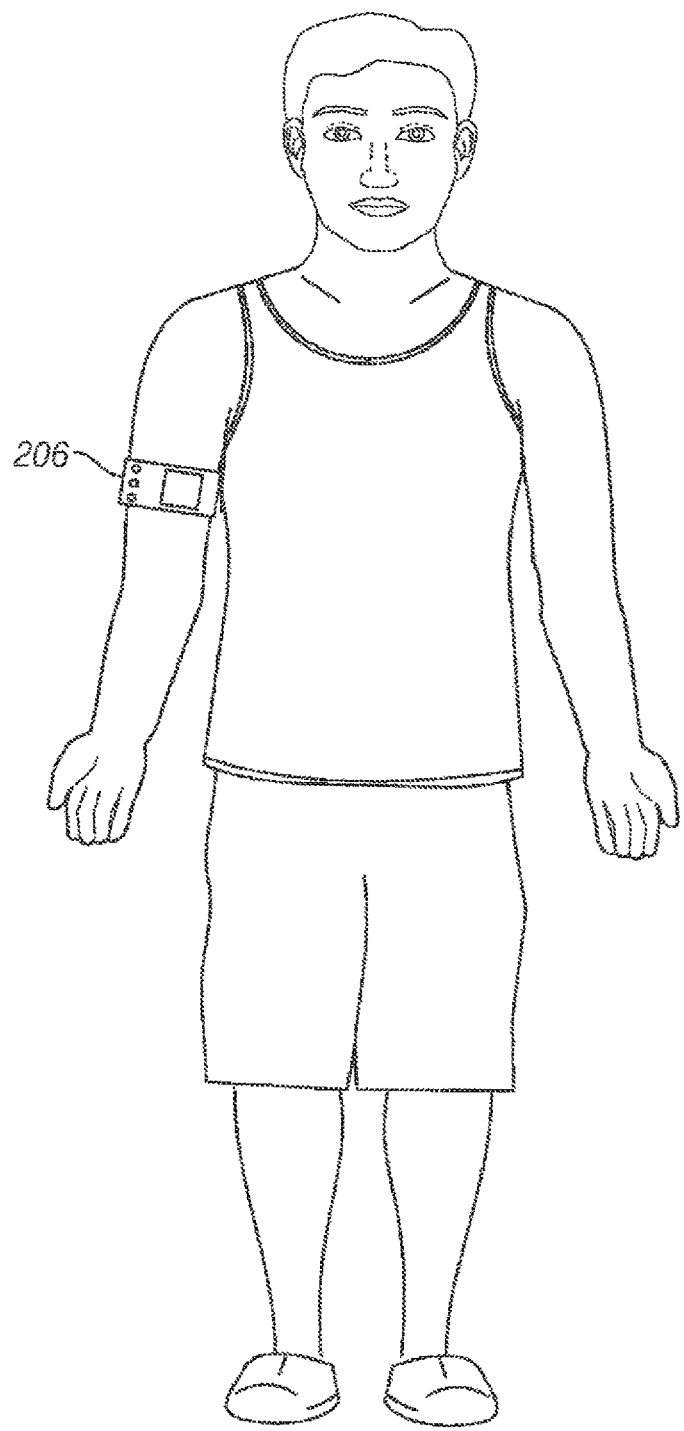
FIG. 9 is a perspective view of an arm mounted fixation device, according to embodiments of the present disclosure.

Alternatively, a second earpiece or ear clip could be provided in conjunction with the tube. As shown in FIG. 8, if a second earpiece is utilized, the two earpieces may be connected via a headset 220 to be worn by the user, the headset either connecting at the top of the user's head or on the back of the head near the user's neck. A carbon dioxide sensor 212 may be mounted on or inside one or more tubes 210 at or near the tips of the tubes to collect and acquire a carbon dioxide expiration reading. One earpiece 200b may house wireless communication functionality such as Bluetooth while the other earpiece 200c has a tube 210 and wiring to carbon dioxide sensor 212 on the tip of the tube 210. The carbon dioxide gas expiration reading is collected by the carbon dioxide sensor 212. The collected data may be transmitted to remote device 300. A visual readout may also be provided, such as a cycle-type computer and receiver device, a computer watch, or a smart phone or PDA-type device which could attach to the user, a fanny-pack, an arm mount fixation device 206 as shown in FIG. 9, or any exercise hardware training equipment, etc. By providing the ability to collect heart rate, oxygen saturation and end tidal carbon dioxide levels, the user can create a calculated $VO_2$ max, or maximal oxygen consumption, which is the user's maximum capacity to transport and utilize oxygen during exercise.

According to embodiments, a "COACHING" feature may audibly reinforce the user if the user falls below a targeted training zone heart rate, for example, along with providing intermittent feedback on training session features (e.g., "TIME", "DISTANCE", "CALORIE CONSUMPTION", "SPEED", "OXYGEN CONSUMPTION", "VO$_2$ Max", etc.). According to embodiments, at least one of interactive device 200 and remote device 300 may facilitate wireless 2-way communication (e.g., walkie-talkie feature), wireless cell phone communication capabilities, wireless radio, satellite radio, analog or digital media playback, along with receiving a variety of wireless transmissions from a smart phone or PDA-like devices, etc. According to embodiments, multiple users having respective interactive devices 200 or remote device 300 may communicate with each other directly or via external device 400. For example, a user may have one-way or two-way communications with a coach, instructor, or other source of information and/or support, wherein the coach, instructor, etc. may receive information gathered by at least one of interactive device 200 and remote device 300. By further example, multiple users may have one-way or two-way communications with each other, such as when multiple users are participants on a team (e.g., baseball, football, soccer, field hockey, ice hockey, etc.). Embodiments could provide communication to hikers, backpackers, cyclists, mountain bikers, mountain climbers and other outdoor enthusiasts via wireless communication such as Bluetooth. The data and communications could include GPS information about the users' locations so lost hikers or backpackers could be easily rescued.

According to embodiments, remote device 300 may be configured to communicate with at least one external device 400. External device 400 may include an information provider, a service-based center, a counselor, an advisor, a coach, a medical professional, an emergency response center, an information database, a personal computing system, a central computing system, a distributed computing system, a server, a communications exchange system, a global navigation satellite system, an entertainment system, a video game console (e.g., Nintendo's Wii, Microsoft's Project Natal for Xbox 360), Web TV, etc., cloud-based entertainment and content stored in data centers, or any intermediary connecting to or between one or more of such points.

According to embodiments, from external device 400, applications, media, software, or other information or data may be retrieved before, during, or after an activity. For example, activity results may be downloaded from remote device 300 to external device 400, for analysis by external device 400. For example, a training program on external device 400 may allow the user to evaluate and/or adjust their exercise training targets based upon data such as the heart rate, end tidal CO$_2$, saturated oxygen and VO$_2$ max signal feedback acquired from the user during prior activity sessions. Connection with external device 400 may include the ability to communicate with Web TV on-air programming such as P90X, spinning class, Tae-Bo, or other training or exercise classes as well as video game challenges through connection with video game consoles. Other features of interactive device 200 or remote device 300 may be customized by the user via external device 400.

According to embodiments, a variety of applications or sub-applications may be provided, each corresponding to separate training program (e.g., running, jogging, walking, cycling, exerciser systems including at home use or health and fitness training facilities using a treadmill, elliptical, stepper, climber, etc.). Applications may be sold or provided separately, downloaded from the internet (e.g., via external remote device 300 or external device 400), provided after the user/purchaser registers their device with the company. After sale marketing or consumer specific access via email, special broadcast offers, etc. may be made directly to the user, with their approval to receive such advertising and promotional messages. For example, a user may periodically receive training tips from the companies advisory board, (e.g., Ex-Olympians, Top Amateurs, Professional athletes, etc.) from around the world. Additionally, "special offers" could be directed to the user from suppliers and/or retailers either in a retail store environment while the user is shopping or shopping alerts offered by web sites such as www.purchaseperks.com, or relating to the activity-type selected by the user, and possibly leading to connectivity to social networks for walkers, runners, cyclists or other relevant groups to learn about events, blog connections, and special offers, etc.

Figure 2:
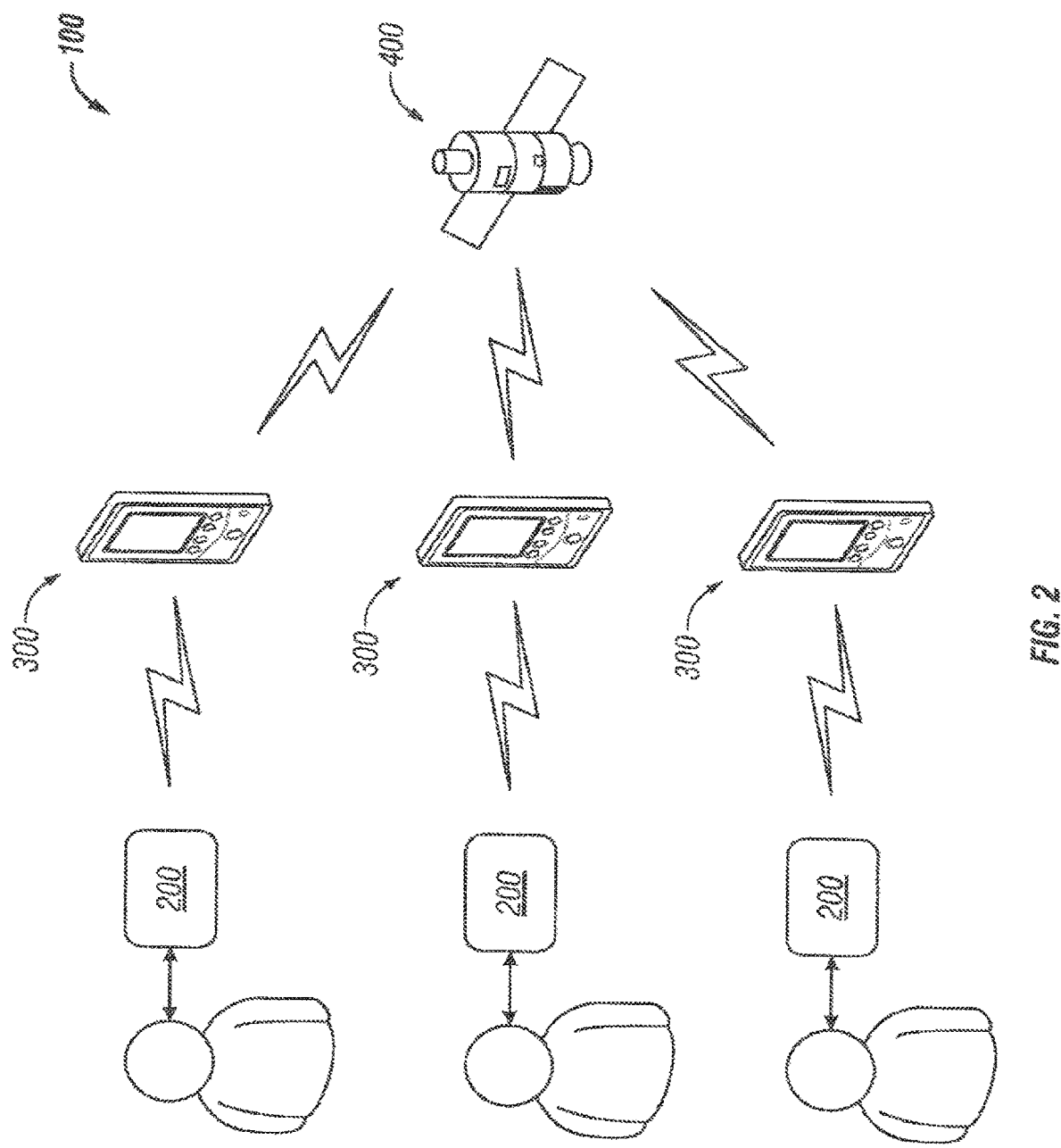
FIG. 2 is a schematic block diagram illustrating various system components configured to operate and communicate as used by a plurality of users, according to embodiments of the present disclosure.

According to embodiments, and as shown in FIG. 2, a plurality of users may each be provided with an interactive device 200, each linking to a respective remote device 300. All of the remote devices 300 may be configured to communicate with a single external device 400, such that information gathered from each of the plurality of interactive devices 200 and remote devices 300 may be collected and analyzed from a single source. Likewise, external device 400 may be configured to transmit information to each of the remote devices 300, each of which, in turn, communicating with the corresponding interactive device 200. Thereby, information gathered from each user or responses generated in response to information gathered from each user may be shared and communicated to all users. The set of users may be defined by a common subscription to a group, service, or plan. According to embodiments, users may exchange information during an exercise activity.

According to embodiments, a plurality of users may be linked to communicate with each other or with a central "coach" via the communications configuration as shown in FIG. 2. Communication may be automated, wherein data generated by the respective components may be exchanged without input from one or more of the plurality of users. Operations supporting such are disclosed further herein. Communication may also be selective, wherein communications, such as voice conversations, may be exchanged among the users.

Figure 3:
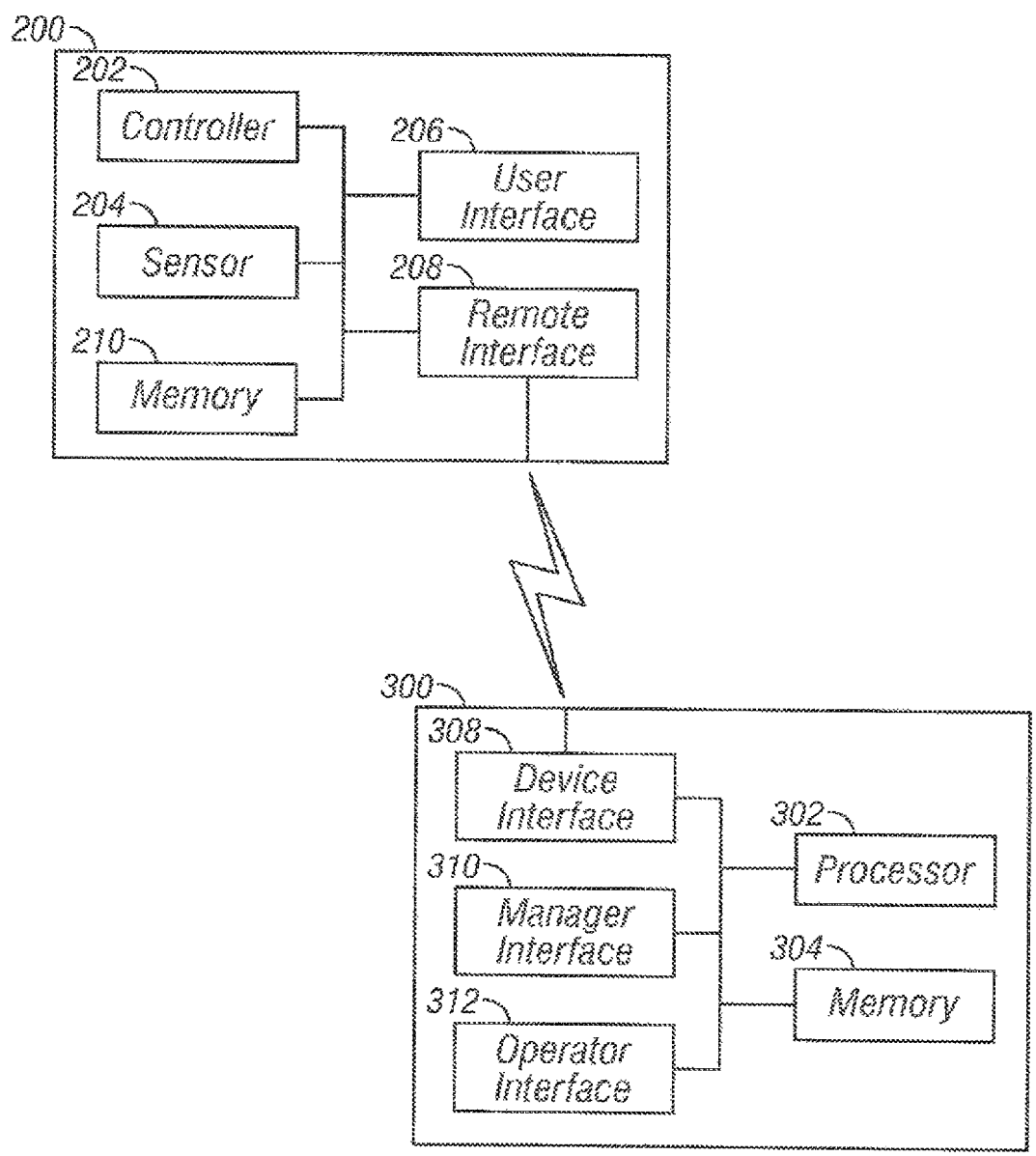
FIG. 3 is a block diagram illustrating the various system components including an interactive device and a remote device, according to embodiments of the present disclosure.

With reference to FIG. 3, a block diagram is provided illustrating the various system components including interactive device 200 and remote device 300 in accordance with one or more embodiments of the present disclosure. Interactive device 200 is shown as including at least one sensor 204, controller 202, memory 210, user interface 206, remote interface 208, and other components as appropriate to produce the desired functionalities of the interactive device 200. Remote device 300 is shown as including device interface 308, manager interface 310, operator interface 312, processor 302, memory 304, and other components as appropriate to produce the desired functionalities of the remote device 300.

In one or more embodiments, sensor 204 may be configured to sense a physiological parameter relating to user 12. Interactive device 200 may obtain data from physiological signals via sensors 204. Sensors 204 may monitor electrical, mechanical, chemical, optical, or other measurable information that contains physiological data of the user and can utilize any source of signals used for physiological events, parameters, or conditions. For example, sensor 204 may comprise a sensor to detect at least one of a user's heart rate, temperature, oxygen saturation, end tidal carbon dioxide, etc. Sensor 204 may be configured to measure metric data apart from physiological parameters, such as intensity of motion, rate of movement, pace of movement, altitude, global positioning, ambient temperature, and other characteristics of the location of the interactive device 200 and/or the user. In one or more embodiments, data obtained by sensor 204 may be provided to controller 202, which suitably analyzes the data, stores appropriate data in memory 210, or provides a response or report as appropriate.

In one or more embodiments, controller 202 may be configured to determine whether a sensed physiological parameter satisfies a notification criteria. Controller 202 may be implemented with any type of microprocessor, digital signal processor, application specific integrated circuit (ASIC), field programmable gate array (FPGA) or other integrated or discrete logic circuitry programmed or otherwise configured to provide functionality as described herein. Controller 202 may execute instructions stored in memory 210 to provide functionality as described herein. Instructions provided to controller 202 may be executed in any manner, using any data structures, architecture, programming language and/or other techniques. Memory 210 is any storage medium capable of maintaining digital data and instructions provided to controller 202 such as a static or dynamic random access memory (RAM), read-only memory (ROM), non-volatile random access memory (NVRAM), electrically erasable programmable read-only memory (EEPROM), flash memory, or any other electronic, magnetic, optical or other storage medium. According to embodiments, interactive device 200 may operate without controller 202, where processor 302 of remote device 300 provides processing and related functions to facilitate operation of interactive device 200.

In one or more embodiments, communication between interactive device 200 and remote device 300 is via remote interface 208 and device interface 308. Remote interface 208 may comprise any unit capable of facilitating wired or wireless data transfer between interactive device 200 and remote device 300, where remote device 300 may comprise a separate device, a programming device, a remote telemetry station, a user-activated device, a mobile handheld unit (e.g., mobile phone, PDA, etc.), a personal computer, an in-home monitoring device, a user-wearable device, an arm mount fixation device, a display device, or any other type of device capable of sending and receiving signals to and from interactive device 200.

Components of remote interface 208 and device interface 308 may be configured to facilitate communication between interactive device 200 and remote device 300. Remote interface 208 and device interface 308 may be configured to perform any type of wired or wireless communication. For example, remote interface 208 and device interface 308 may send and receive radio frequency (RF) signals, infrared (IR) frequency signals, or other electromagnetic signals. Any of a variety of modulation techniques may be used to modulate data on a respective electromagnetic carrier wave. Alternatively, wired communications may also occur between interactive device 200 and remote device 300. Communications protocols for managing communication between remote interface 208 and device interface 308 are known, and may include IEEE 802.11, IEEE 802.3, USB-compatible, Bluetooth, etc.

In one or more embodiments, user interface 206 of interactive device 200 or manager interface 310 of remote device 300 may be configured to communicate with the user. For example, user interface 206 or manager interface 310 may notify the user regarding metric values relating to a sensed physiological parameter (e.g., an audio speaker device, a tactile vibrating device, or other output device). Notifications may be received by the user via any one of the senses. For example, user interface 206 may include an audio speaker, where at least a portion of interactive device 200 is within sufficient proximity of the ears of a user to generate an audible message. User interface 206 or manager interface 310 may include a display for conveying messages to a user.

User interface 206 or manager interface 310 may include an input device that allows data, commands or selections to be input into interactive device 200 or remote device 300 by a user. User interface 206 or manager interface 310 may include, but is not limited to, at least one of the following: a keyboard, keypad, track ball, mouse, touch-sensitive displays, push buttons, magnetic readers, RF readers, tablets, styluses, microphones, voice recognizers, handwriting recognizers and any other device that allows a user to input data.

In one or more embodiments, processor 302 may be configured to perform functions of remote device 300 as described herein. Processor 302 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 302 may execute instructions stored in memory 304 to provide functionality as described herein. Instructions provided to processor 302 may be executed in any manner, using any data structures, architecture, programming language and/or other techniques. Memory 304 is any storage medium capable of maintaining digital data and instructions provided to processor 302 such as a static or dynamic random access memory (RAM), read-only memory (ROM), non-volatile random access memory (NVRAM), electrically erasable programmable read-only memory (EEPROM), flash memory, or any other electronic, magnetic, optical or other storage medium.

In one or more embodiments, data may be recorded in memory 304 for later transmission during communication with external device 400. Such data may include physiological parameters sensed by interactive device 200, performance statistics of a user during operation of at least interactive device 200, or other metrics sensed by interactive device 200 or remote device 300.

Remote device 300 may further include operator interface 312 for connecting remote device 300 to at least external device 400. Operator interface 312 may facilitate communication with an external device 400 over communication networks, phone lines, wireless devices, public switched telephone network, airwaves, etc. Configurations, standards, and protocols for facilitating such communication may include cellular telephone networks, public switched telephone network (PSTN), code division multiple access (CDMA), time division multiple access (TDMA), frequency-division multiple access (FDMA), global system for mobile communications (GSM), IEEE 802.11, IEEE 802.3, etc. Data may be exchanged between remote device 300 and external device 400, such as instructions, tutorials, audio files, etc. According to embodiments, device interface 308 and operator interface 312 may be consolidated into one device and set of protocols that provide the desired connections. According to embodiments, exercise and communications system 100 may be configured to utilize a communications network (e.g., OnStar) with appropriate interfacing configurations to sustain two-way communication with external device 400.

According to embodiments, one or both of interactive device 200 and remote device 300 may be configured to provide enhanced features with additional components. For example, one or both of interactive device 200 and remote device 300 may include a GPS device, AM/FM radio circuitry, digital radio circuitry, or satellite radio circuitry. According to embodiments, such components may be provided in addition to or in combination (integrated) with components disclosed above.

According to embodiments, a series of operations may be performed by at least one of interactive device 200 and remote device 300, or a combination of the two. According to embodiments, an exercise mode may be determined in operation 510, wherein the exercise mode has predetermined or customizable criteria, as disclosed herein. The exercise mode may be customizable or selectable by a user via at least one interface with at least one of interactive device 200, remote device 300, and external device 400. According to embodiments, criteria associated with a given exercise mode may be determined in operation 512.

Figure 4:
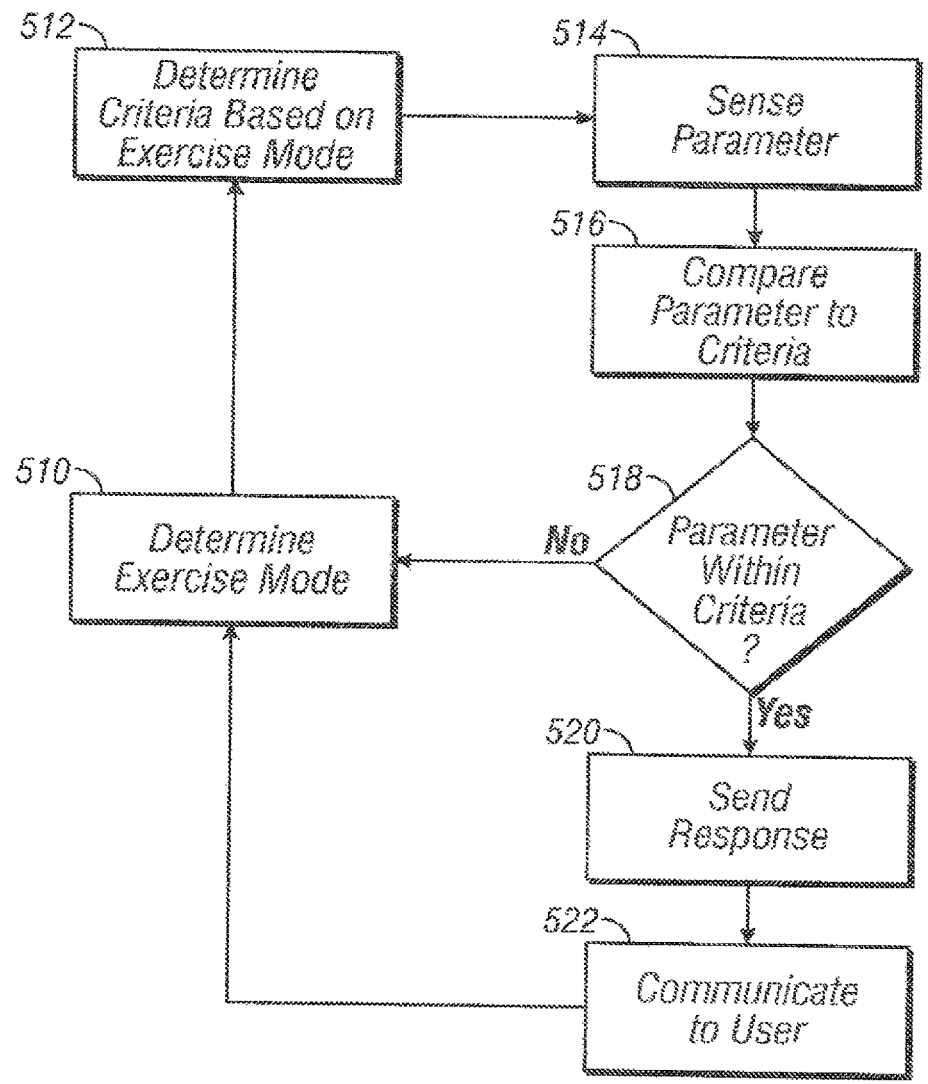
FIG. 4 is an operational flow diagram illustrating a process for operating at least one of an interactive device and a remote device, according to embodiments of the present disclosure.

According to embodiments, a parameter may be sensed in operation 514, as disclosed herein. In operation 516, the parameter may be compared to the criteria associated with the exercise mode. If the parameter is determined to be within the criteria, then a response may be generated in operation 520. The response may be any action taken by interactive device 200 or remote device 300 that is predetermined based on the criteria, as disclosed herein. The response may include an alteration made to the activity or environment of the user, as disclosed herein. The response may result in a communication being provided to the user in operation 522, as shown in FIG. 4. For example, a status update, motivational message, or other communication may be provided to the user by at least one of interactive device 200 and remote device 300. Where the parameter is determined to not be within the criteria, then the response may be bypassed, or a different response may be provided corresponding to the parameter not being satisfied.

In various embodiments, an integrity management system is operational in an IT infrastructure or with numerous other general purpose or special purpose computing system environments or configurations or other complex systems. Examples of well known computing systems, environments, and/or configurations that may be suitable for use with the invention include, but are not limited to, personal computers, server computers, hand-held or laptop devices, notebooks, iPads, multiprocessor systems, microprocessor-based systems, set top boxes, programmable consumer electronics, network PCs, minicomputers, mainframe computers, telephony systems, Web TV, distributed computing environments that include any of the above systems or devices, and the like.

The integrity management system may be described in the general context of computer-executable instructions, such as program modules, being executed by a computer. Generally, program modules include routines, programs, objects, components, data structures, etc. that perform particular tasks or implement particular abstract data types. The system may also be practiced in distributed computing environments where tasks are performed by remote processing devices that are linked through a communications network. In a distributed computing environment, program modules may be located in both local and remote computer storage media including memory storage devices. The computer programs are stored in a memory medium or storage medium or they may be provided to a processing unit through a network or I/O bus.

In one aspect, the integrity management system includes at least one central processing unit (CPU) or processor. The CPU can be coupled to a memory, ROM or computer readable media containing the computer-executable instructions for generating and using fingerprints for integrity management. Computer readable media can be any available media that can be accessed by the system and includes both volatile and nonvolatile media, removable and non-removable media implemented in any method or technology for storage of information such as computer readable instructions, data structures, program modules or other data. Computer storage media includes, but is not limited to, RAM, ROM, EEPROM, flash memory, portable memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the fingerprint generation and matching systems. Communication media typically embodies computer readable instructions, data structures, program modules or other data in a modulated data signal such as a carrier wave or other transport mechanism and includes any information delivery media. By way of example, and not limitation, communication media includes wired media such as a wired network or direct-wired connection, and wireless media such as acoustic, RF, infrared and other wireless media. Combinations of any of the above should also be included within the scope of computer readable media. The computer readable media may store instructions and/or data which implement all or part of the system described herein.

The process described above can be stored in a memory of a computer system as a set of instructions to be executed. In addition, the instructions to perform the processes described above could alternatively be stored on other forms of machine-readable media, including magnetic and optical disks. For example the processes described could be stored on machine-readable media, such as magnetic disks or optical disks, which are accessible via a disk drive (or computer-readable medium drive). Further, the instructions can be downloaded into a computing device over a data network in a form of compiled and linked version.

Alternatively, the logic to perform the processes as disclosed above could be implemented in additional computer and/or machine readable media, such as discrete hardware components as large-scale integrated circuits (LSI's), application-specific integrated circuits (ASIC's), firmware such as electrically erasable programmable read only memory (EEPROM's); and electrical, optical, acoustical and other forms of propagated signals (e.g., carrier waves, infrared signals, digital signals, etc.).

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms-even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

What is claimed is:

1. A system comprising an interactive device and a remote device, wherein the interactive device comprises in combination one or more sensors, a memory, a user interface, a controller configured to determine whether a sensed physiological parameter satisfies a predetermined criteria, and a remote interface wherein the interactive device and remote device are separate while maintaining a communications link, or are integrated into a single housing:
    (i) Wherein the one or more sensors are configured to sense at least one physiological parameter of a user during an activity, the physiological parameter being at least one of heart rate, oxygen saturation, and end tidal carbon dioxide;
    (ii) Wherein the remote interface is configured to communicate data corresponding to the at least one physiological parameter to the remote device during the activity, and further configured to receive from the remote device a response corresponding to the at least one physiological parameter, wherein the response is determined by the remote device based on whether the at least one physiological parameter is within predetermined criteria; and
    (iii) Wherein the user interface is configured to communicate the response to the user,
    wherein the interactive device is integrated into a housing configured to be disposed within an ear of the user, said housing further comprising a sensor mounted on a tube extending from the housing and configured to locate the sensor in front of a mouth of the user when said housing is disposed within the ear of the user, and
    wherein the user interface includes an input device that allows data or commands to be input into interactive device or remote device by a user, and wherein the user interface includes at least one of a keyboard, keypad, and voice recognizer, and
    wherein the user interface comprises a display for conveying messages to a user, and wherein the user interface includes an audio speaker that can generate an audible message that is of sufficient proximity to ear of a user, and
    wherein the display or audio speaker notifies user regarding metric values relating to a sensed physiological parameter,
    (iv) Wherein the controller acquires data obtained by sensor of Interactive Device, and wherein the controller stores the data in memory of Interactive Device, and
    wherein the controller is configured to receive instructions stored in the memory, and wherein the controller responds by providing a report to user regarding whether the sensed physiological parameter satisfies the predetermined criteria;
    wherein the remote device comprises a device interface, and a memory,
    wherein the remote device comprises one or more of a watch, a cell phone, a personal digital assistant (PDA), smart phone, and an arm mounted device,
    wherein the remote device further comprises a software application (app), wherein the software application comprises a training program that allows the user to evaluate or adjust exercise training targets based upon physiological data such as heart rate, end tidal $CO_2$, saturated oxygen, or uses temperature, wherein said data are acquired from the user, and wherein the software application has a predetermined or user-determinable set of target goals and a predetermined or user-determinable safe range of physiological parameters, and wherein the software application is stored by said interactive device.

2. The interactive device of claim 1, in combination with a remote device and a device interface, wherein the device interface is configured for wired communication between interactive device and remote device.

3. The interactive device of claim 1, in combination with a remote device and a device interface, wherein the device interface is configured for non-wired communication between the interactive device and remote device.

4. The interactive device of claim 1, in combination with a remote device and a device interface, wherein the device interface is configured for non-wired communication between the interactive device and remote device, wherein said non-wired comprises one or more of radio frequency (RF) signals, infrared (IR) frequency signals, or acoustic signals.

5. The interactive device of claim 1, in combination with an external device.

6. The interactive device of claim 1, in combination with an external device, wherein the external device comprises an entertainment system, a video game console, or a web TV.

7. The interactive device of claim 1, wherein said one or more sensors comprises a pulse oximeter device configured to obtain heart-rate from a finger or ear lobe of a user.

8. A method performed by a remote device in data communication with an interactive device, wherein the interactive device comprises in combination one or more sensors, a memory, a user interface, a controller, and a remote interface, wherein the one or more sensors are configured to sense at least one physiological parameter of a user being at least one of heart rate, oxygen saturation, and end tidal carbon dioxide, and wherein the remote device comprises a device interface, and a memory, the controller being configured to determine whether a sensed physiological parameter satisfies a predetermined criteria;

wherein the interactive device and remote device are separate while maintaining a communication link, or are integrated into a single housing, wherein the remote device comprises one or more of a watch, a cell phone, a personal digital assistant (PDA), smart phone, and an arm mounted device, wherein the remote device further comprises a software application (app), wherein the software application comprises a training program that allows the user to evaluate or adjust exercise training targets based upon physiological data such as heart rate, end tidal $CO_2$, saturated oxygen, or user's temperature, wherein the software application has a predetermined or user-determinable set of target goals and a predetermined or user-determinable safe range of physiological parameters, and wherein the remote interface, is configured to communicate data corresponding to the at least one physiological parameter to a remote device during the activity, and further configured to receive from the remote device a response corresponding to the at least one physiological parameter, wherein the response is determined by the remote device based on whether the at least one physiological parameter is within predetermined criteria; and wherein the user interface is configured to communicate the response to the user, wherein the interactive device is integrated into a housing configured to be disposed within an ear of the user, said housing further comprising a sensor mounted on a tube extending from the housing and configured to locate the sensor in front of a mouth of the user when said housing is disposed within the ear of the user, and wherein the user interface includes an input device that allows data or commands to be input into interactive device or remote device by a user, and wherein the user interface includes at least one of a keyboard, keypad, and voice recognizer, and wherein the user interface comprises a display for conveying messages to a user, and wherein the user interface includes an audio speaker that can generate an audible message that is of sufficient proximity to ear of a user, and wherein the display or audio speaker notifies user regarding metric values relating to a sensed physiological parameter, wherein the controller acquires data obtained by sensor of Interactive Device, and wherein the controller stores the data in memory of Interactive Device, and wherein the controller is configured to receive instructions stored in the memory, and wherein the controller responds by providing a report to user regarding whether the sensed physiological parameter satisfies the predetermined criteria;

wherein said data are acquired from the user, and wherein the method comprises:

(i) Determining a selected exercise mode, wherein the selected exercise mode is selected by a user from among a plurality of exercise modes;

(ii) Receiving, from the interactive device, data corresponding to a parameter sensed by the interactive device;

(iii) Comparing the data to a predetermined criteria or to predetermined target goal associated with the selected exercise mode;

(iv) Selecting a predetermined response based on whether the data are within the criteria associated with the selected exercise mode; and (v) Transmitting the predetermined response to the interactive device, whereby the predetermined response is communicated to the user via the interactive device.

9. The method of claim 8, wherein the predetermined response is communicated to the user via an audio output device of the interactive device.

10. The method of claim 8, wherein the parameter sensed by the interactive device corresponds to a physiological parameter of the user.

11. The method of claim 8, wherein the parameter sensed by the interactive device corresponds to a physiological parameter of the user, and wherein the physiological parameter is at least one of heart rate, temperature, oxygen saturation, user's temperature, and end tidal carbon dioxide.

12. The method of claim 8, wherein the remote device and interactive device are integrated into a single housing configured to be disposed within an ear of the user.

13. The method of claim 8, further comprising:

(i) Transmitting the data corresponding to the parameter to an external device;

(ii) Retrieving associated responses and criteria from an external device; or (iii) Transmitting the data corresponding to the parameter to an external device and also retrieving associated responses and criteria from an external device.

14. The method of claim 13, whereby the external device distributes at least one of the data corresponding to the parameter and a response to at least one other user.

15. The method of claim 8, wherein the predetermined response is communicated to the user via an audio output device of the interactive device, wherein the interactive device comprises a GPS device, and wherein the GPS device provides audio message alerts for training zone high and low limits.

16. The method of claim 8, wherein the exercise mode is running, jogging, walking, swimming, or cycling.

* * * * *